US005642542A

United States Patent [19]

Kometani

[11] Patent Number: 5,642,542

[45] Date of Patent: Jul. 1, 1997

[54] PORTABLE APPARATUS FOR SUPPORTING A PATIENT FOR MASSAGE TREATMENT

[76] Inventor: George Kometani, 12429 Stanwood Pl., Los Angeles, Calif. 90066

[21] Appl. No.: 646,038

[22] Filed: May 7, 1996

[51] Int. Cl.[6] ................................ A47B 7/00; A61F 5/00

[52] U.S. Cl. .......................... 5/620; 5/600; 5/624; 5/613; 606/242; 606/243

[58] Field of Search ................................ 5/620, 621, 622, 5/624, 600, 613, 657, 652, 181; 297/423.11, 423.12; 601/23, 24; 606/241, 242, 243

[56] References Cited

U.S. PATENT DOCUMENTS

| | | | |
|---|---|---|---|
| 938,172 | 10/1909 | Schutz | 297/423.11 |
| 3,949,983 | 4/1976 | Tommasino | 5/600 |
| 4,333,638 | 6/1982 | Gillotti | 5/620 |
| 4,391,438 | 7/1983 | Heffington | 5/621 |

FOREIGN PATENT DOCUMENTS

| | | | |
|---|---|---|---|
| 731459 | 9/1932 | France | 5/613 |

*Primary Examiner*—Flemming Saether
*Attorney, Agent, or Firm*—Beehler & Pavitt

[57] ABSTRACT

Portable apparatus to be carried and set up at selected locations and taken down by a masseur or physical therapist, comprising a basic frame having downwardly extendable legs and formed by parallel co-extensive side members held together by a first rigid transverse bar secured at corresponding ends of the side members, and a second such bar secured at a preselected distance from each of the other ends of side members to leave trailing free end portions from which extend a plurality of upwardly projecting elements. A pendant knee support may extend below the trailing free ends of the side members and the intermediate transverse bar, and/or a lower body support may be attached to the ends of the trailing members. A face support desirably is provided to extend from the first transverse bar and the inner areas defined by the frame, and the lower body support may be provided with sheet or mesh material supported around its edges. Cushions may be provided for the face support and frame defined areas.

10 Claims, 4 Drawing Sheets

Fig. 3
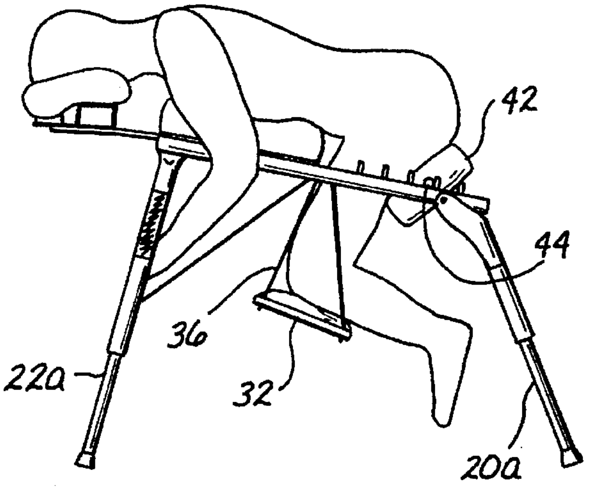
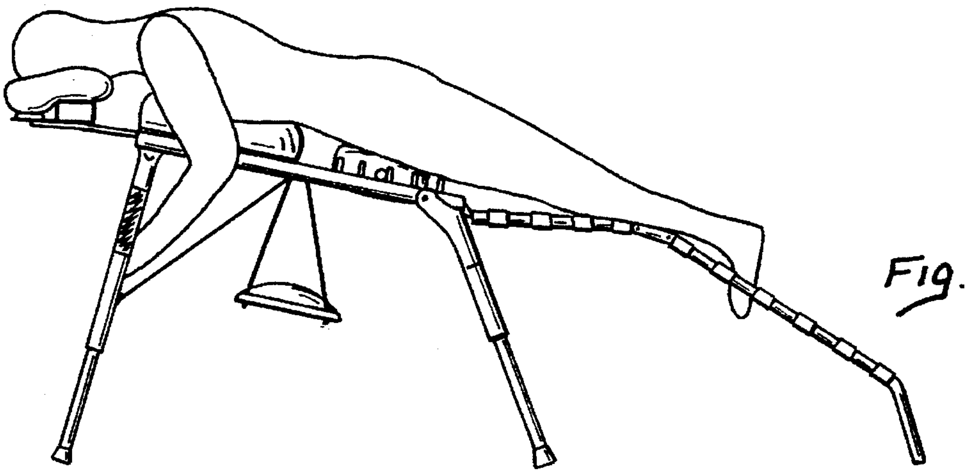
Fig. 4
Fig. 5
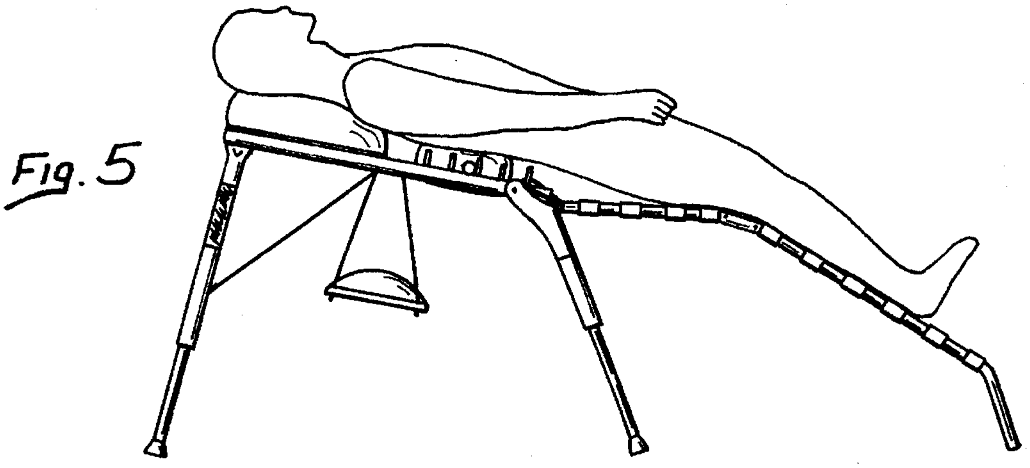

PORTABLE APPARATUS FOR SUPPORTING A PATIENT FOR MASSAGE TREATMENT

FIELD OF THE INVENTION

This invention relates to a type of medical apparatus employable for patient support in several positions, and particularly for massage, bodywork or other physical therapy treatment.

BACKGROUND OF THE INVENTION

When a patient is being given a massage, bodywork or other physical therapy treatment in a hospital, clinic or a doctor's or practitioner's office, the patient may be placed on any one of a number of different, permanent supports which may be set up in such establishment. The support chosen may be fixed, but adjustable for the size of the patient, as well as the height of the person engaging in the massage, bodywork or other physical therapy treatment. Examples of such permanent or fixed types of patient supports may be seen in the following United States patents: U.S. Pat. Nos. 4,391,438; 4,398,707; 4,662,361; 4,746,167; 5,401,078; and 5,487,590.

While many persons may go to an establishment in order to receive a massage, bodywork or similar type of physical therapy, many others, particularly those in executive or other stressful employments, may feel that they are not in a position to take the time to visit an establishment in order to obtain a massage. Such latter persons, however, may desire massage treatments, if administered in their offices or at some other places of their employments. Thereby, such individuals may not lose the time it takes to travel to and from a massage establishment, but they may be willing to give up a relatively short period of time, such as ten (10) minutes to half an hour, in order to receive a massage to relieve some of their job tensions and stresses—particularly where, in some situations, they may engage in dictating or telephone conversations while being massaged. The needs of these busy individuals have been satisfied by visiting masseurs who may arrive at a subject's office by appointment, and set up to provide a massage in the office of the subject, or at some other location at the place of employment.

While some types of massages may be administered to a subject in almost any position, desirably the subject should sometimes be placed on a type of table, or in some special seated or prone orientation. This requires the masseur to bring with him or her some type of portable support on which the subject may be placed. To this end, various types of portable tables or supports have been devised, but none has been found suitable for placing the subject in several different orientations, so that the most effective massage treatments can be administered.

Another problem has been that, portable massage tables heretofore available, have been of a standard size and height. Where the masseur is tall, he or she may be able to effect a proper massage with the subject placed on such a table. However, where the masseur may be short in height, it may be difficult for the masseur to administer an effective massage if the subject is disposed on a high table.

It is also important that, for a traveling masseur, the apparatus which he or she carries into a subject's office, home or other location, be light enough in weight so as not to make transporting the apparatus a difficult and uncomfortable task.

SUMMARY OF THE INVENTION

The apparatus of the present invention is light in weight and unfolds from a convenient closed position to a position which enables the subject of a massage to be comfortably supported in a knee bent position in which the subject may be either inclined, erect or prone, depending upon the type of treatment which is to be administered. In addition, a lower body extension may be detachably provided to enable the subject to be supported in either a supine position or completely prone.

The core of the apparatus is a frame which defines a forward trapezoidal area covered by a canvas or other planar sheetlike support. The frame is preferably constructed of two side members which may angle toward each other or be parallel and are disposed in a common horizontal plane. The forward ends of the side members are joined to the ends of a first transverse element. A second transverse element, parallel to the first, and spaced from the latter, is also secured to the two side members, but intermediately between the opposite ends of the side members, thereby leaving a portion of each side member extending rearwardly behind the trapezoidal area. Each of these extended portions of the side members is provided with a plurality of upwardly extending retaining elements or projections, similarly spaced from each other.

The forward transverse member desirably may be orificed to receive and support rods to carry a forwardly extending face or head rest.

Each of the forward corners formed by the intersection of an end of the first transverse member with the forward end of a side member is provided with a leg which may be pivoted from a first position substantially parallel to the side member to a second downward position substantially normal to its side member. A hand gripping transverse member may be provided to extend between the two legs at a preselected distance from the corner about which the leg is pivoted. A second pair of legs is provided, with each being pivotably secured to an end of one of a side member extension to pivot between a first position substantially parallel to a side member and a second downwardly extending position.

A rectangular knee support may be hung by flexible cable loops over the second transverse member between side members, each end of the cable being attached to a different corner of the knee support.

In addition, a rotatable cushion may be provided in a convexed rectangular form to extend between the rear extensions of the side members. This cushion may be supported by a cylindrical shaft extending axially through the cushion and projecting from each end, so that the shaft may be laid on both side member extensions between adjacent pairs of the upwardly extending elements or projections. Cushions are desirably provided to cover not only the trapezoidal planar support, but also the face or head rest extending from the forward end of the frame.

Each of the foldable legs desirably has a telescoping capability so that the height of the frame may be raised or lowered to a limited extent.

In order that the apparatus may not only support a patient on his or her knees in either an inclined, erect or upper body prone position, there is also provided a slightly arched lower body support member formed by a pair of parallel side members which may be held in their parallel disposition by fixedly secured rigid parallel transverse members spaced apart from each other. The side members may be interconnected by a number of parallel straps which are looped over the side members. Alternatively, a nylon mesh sheet could be suspended from the side and transverse members. The forward end of each of these arched members is provided with endless loops or cables, each of which may be hooked over any number of upwardly extending elements or projections adjacent the end of a rearwardly extending side member, to adjust the height of the support member.

It will be found that the complete apparatus may be readily folded up for carrying and, if the various frame members are fabricated of aluminum, or even of a light, rigid, plastic, the entire apparatus may weigh less than 15 pounds for convenient carrying by the masseur. The masseur may set the apparatus quickly up in a temporary location, and remove it therefrom after the massage session in a subject's office or other temporary location has been completed.

DESCRIPTION OF THE DRAWINGS

In the accompanying drawings,

FIG. 3 is a side elevation illustrating the use by a patient of the basic frame portion shown in FIG. 2, with cushions.

FIG. 4 is a side elevation showing use of the apparatus illustrated in FIG. 1, with the patient in a prone position.

FIG. 5 is similar to FIG. 4 but illustrating how the apparatus may be used to accommodate a patient in a supine position.

DESCRIPTION OF THE PREFERRED EMBODIMENT

Figure 1:
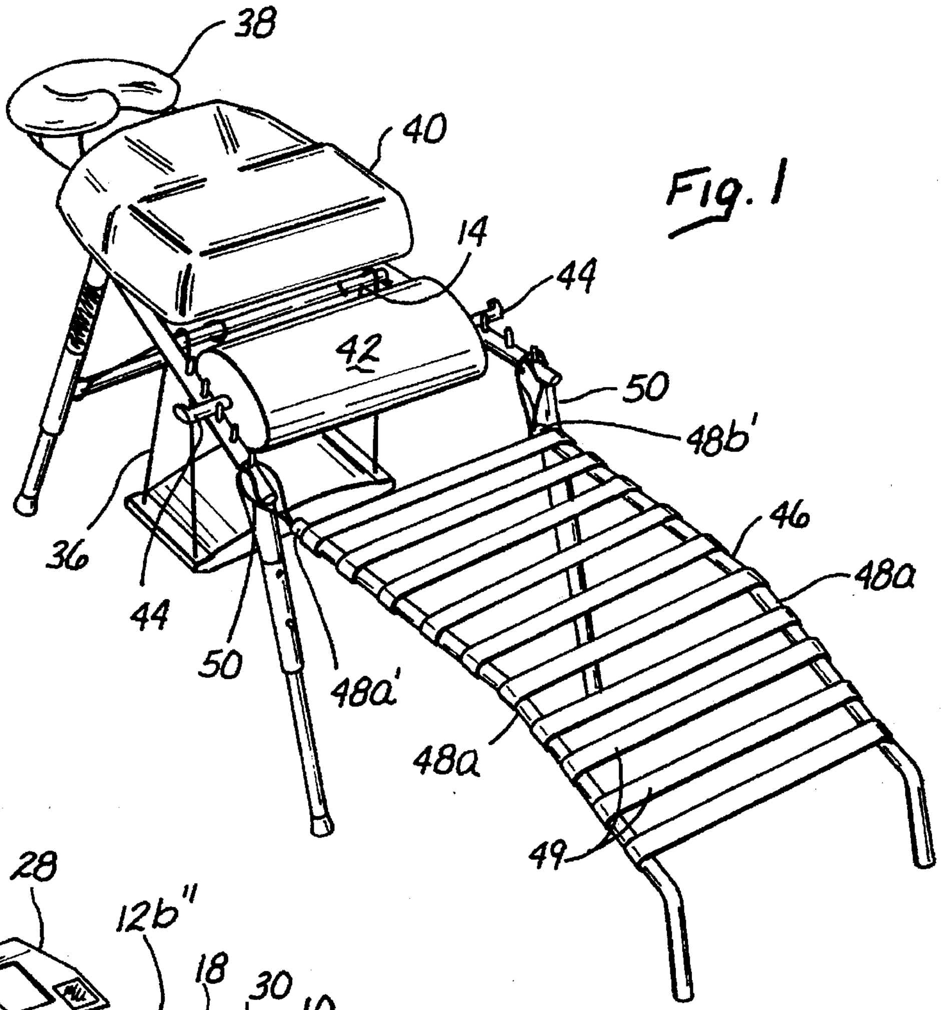
FIG. 1 is a perspective view of the complete apparatus of the present invention.

The core of the present invention is the frame 10 which is formed of a pair of side members **12*a* and 12*b*, slightly angled toward each other in the same plane with their ends after 12*a*' and 12*b*' spaced apart from each other by a greater distance than the spacing between their forward ends 12*a*" and 12*b*". The forward ends 12*a*" and 12*b*" are held together by a transverse member 14 (FIG. 6) secured to both those ends, and by a second transverse member 16 which is parallel to the member 14, but spaced therefrom and joined to the side members 12*a* and 12*b* intermediate the lengths thereof to leave after segments 12*a*'" and 12*b*'" extending rearwardly from where the transverse member 16 is secured to the side members 12*a* and 12*b*. The result of joining the forward portions of the side members 12*a* and 12*b* of the transverse members 14 and 16 is to define a trapezoidal area 18**.

Legs **20*a* and 20*b* are hinged adjacent the after ends 12*a*' and 12*b*' of the side members 12*a* and 12*b*, respectively. Each of the legs 20*a* and 20*b* is adapted to pivot between the downward position shown in FIGS. 1–5 and a retracted position shown in FIGS. 6 and 7. In this second position, legs 20*a* and 20*b* may be in parallel abutment with the side members 12*a* and 12*b*, respectively. Legs 22*a* and 22*b* are hinged adjacent the forward ends 12*a*" and 12*b*" of the side members 12*a*, 12*b* respectively to pivot between the extended position shown in FIGS. 1–5 and the retracted position shown in FIG. 6 and 7. A cross member 24 which may serve as a hand gripping member, may be secured parallel to the transverse member 14 at intermediate points on the legs 22*a* and 22*b*. The height of each of the legs 20*a*, 20*b*, 22*a* and 22*b***, may be varied by limited telescoping in a manner long well known and, as such, employed in adjustable height crutches.

A plurality of upwardly extending elements 26 spaced from each other are provided on the after segments **12*a*'" and 12*b*'" portions of the side members 12*a* and 12*b*. The elements 26 on the after segments 12*a*'" of the side member 12*a* desirably should be disposed and spaced from each other in the same manner as the elements 26 on the after segment 12*b*'" of the side member 12*b***.

For the comfort of the patient, a face support member 28 may be provided to extend forwardly of the transverse member 14 and secured to the latter. A canvas of plastic sheet 30 may be provided to cover most of the trapezoidal area 18.

A preferably rectangular member 32 having cushioning 34 is suspended from the ends of the transverse member 16 by a flexible cable or rope 36 secured to each end of the rectangular member 32. The cable may be looped over any number of upwardly extending elements 26 on the after segments **12*a*'" and 12*b*'" of the side members 12*a*, 12*b*, to enable the height of member 32** to be adjusted.

For the comfort of the patient or other subject of the massage, a slightly open face cushion 38 may be disposed on the face support 28, a cushion 40 may be placed over the canvas or plastic sheet 30, and a movable cushion 42 formed around an axle 44 is provided for disposition between the after segments **12*a*'", 12*b*'" of the side members 12*a*, 12*b*, respectively with its axle 44 being disposed between similar pairs of upstanding elements 26 on the after segments 12*a*'" and 12*b*'" of the side members 12*a* and 12*b***.

While the apparatus thus far described may be utilized for certain body positions of the patient or subject which the masseur may desire for working on the patient or subject, such as a kneeling position, it is also desirable to provide a lower body support 46 formed by a pair of arched members **48*a*, 48*b* which are spaced apart from each other and carry a plurality of parallel straps 49, also spaced from each other. The forward ends 48*a*' and 48*b*' of these arched members 48*a* and 48*b* may be provided with cable loops 50. Attaching the lower body support 46 to the after ends 12*a*' and 12*b*' of the side members 12*a* and 12*b* by looping the cable 50 at the forward ends 48*a*' and 48*b*' of the arched members 48*a* and 48*b* over any number of upwardly extending elements 26 on the after segments 12*a*'" and 12*b*'" of the side members 12*a* and 12*b* adjusts the height of the lower body support member 46**, enabling the masseur to have the patient or subject assume a fully prone or supine position for different treatments.

It should also be pointed out that, in most uses of the apparatus, it is desirable to place the cushion 42 transversely of the after segments **12*a*'" and 12*b*'" of the side members 12*a* and 12*b*. Thus, in the kneeling position of the patient or subject, the cushion 42 may serve as a seat support as shown in FIG. 3, while in the prone or supine positions of the patient or subject, as shown in FIGS. 4 and 5, the cushion 42** may serve as a hip or abdomen support or a back support, respectively.

Figure 2:
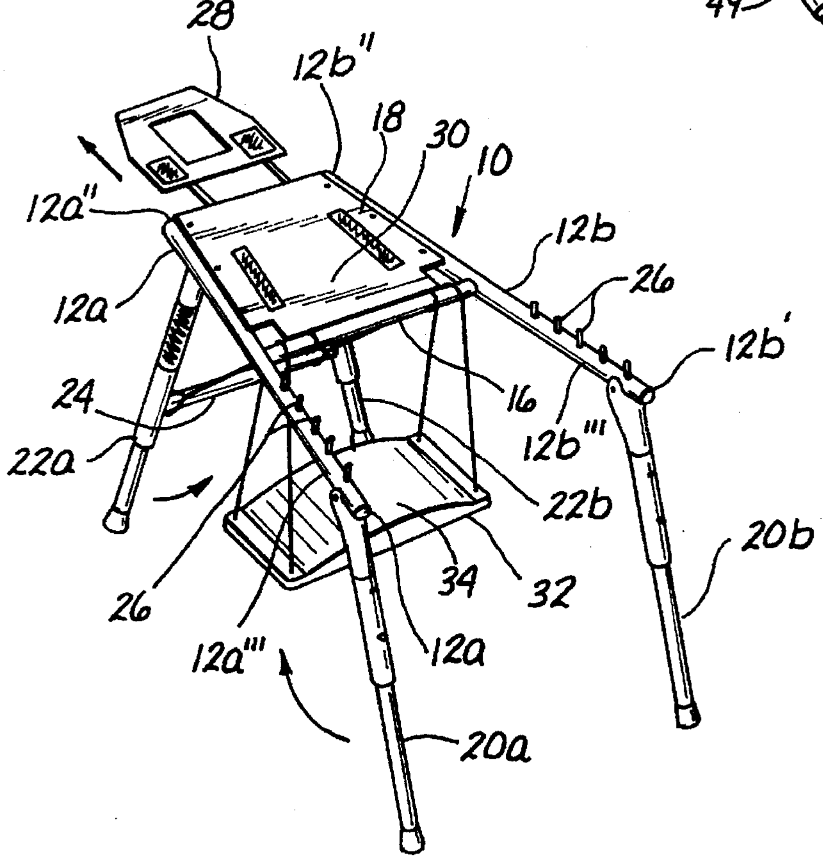
FIG. 2 is a perspective view of the basic frame portion of the apparatus which is shown in FIG. 1.
Figure 8:
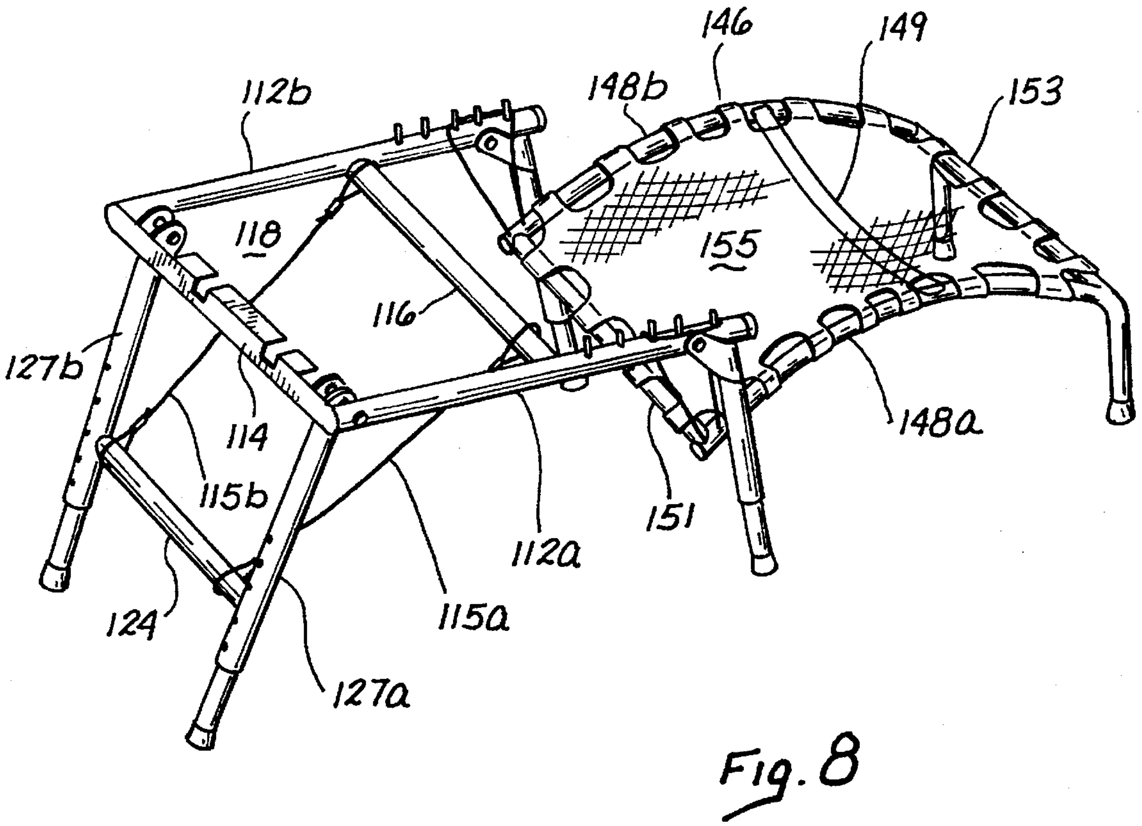
FIG. 8 is a perspective view of the frame members of a slightly modified embodiment of the present invention.

In the alternative embodiment of the invention shown in FIG. 8, the side members **112*a*, 112*b* are held in parallel by the transverse members 114 116, thereby defining a rectangular area 118 instead of the trapezoidal area shown in FIG. 2. In addition, a pair of flexible cables 115*a*, 115*b* are provided between the transverse member 116 and the cross bar 124 to limit the angle to which the legs 127*a*, 127*b* may be swung down from their folded-up positions against side members 112***a* 112*b*, respectively,.

Lastly, the lower support member 146 is slightly modified in FIG. 8 to the extent that the side members 148*a*, 148*b* are held in fixed spaced relationship to each other by transverse members, 151, 153 which are secured at each of their ends to one of a side member 148*a*, 148*b*. In lieu of the support straps 49 shown in FIG. 1, one strap 149 may be employed to support a nylon or other type mesh 155, the edges of which may be secured to the side members 148*a*, 148*b*, or to such side members and the transverse members 151, 153.

The FIG. 8 embodiment thus described and so illustrated may otherwise employ the knee support 28 and the cushions 38, 40 and 42 of the FIGS. 1, 2, 6 and 7 embodiments described above.

Thus, it may be seen that the apparatus of the present invention may provide comfortable support for a patient or subject in the several positions in which the patient or subject would ordinarily be placed by the masseur.

Figure 6:
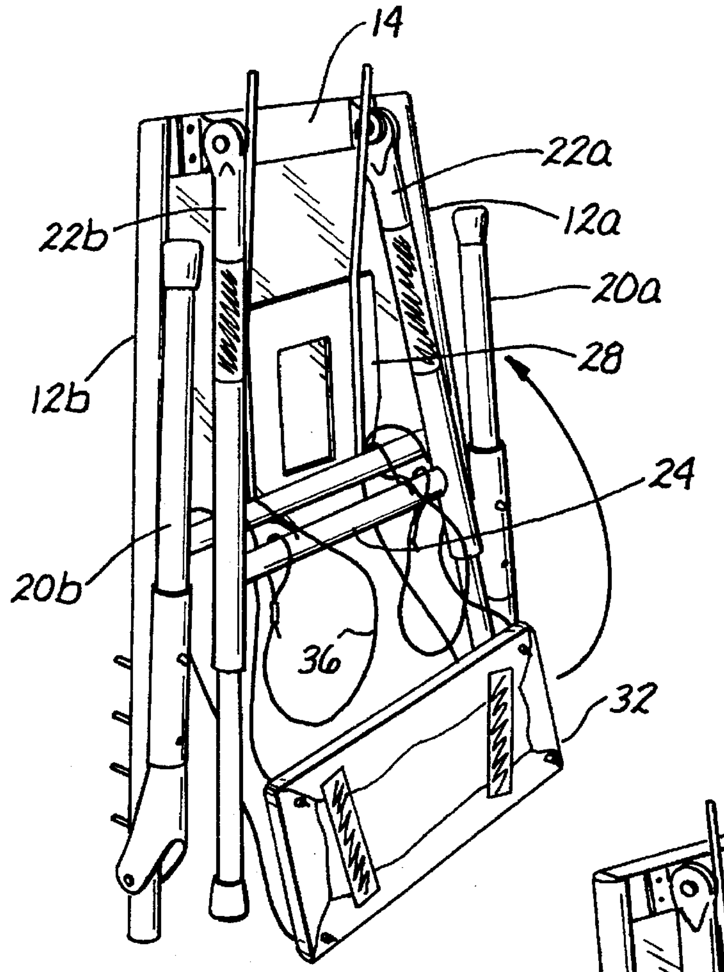
FIG. 6 shows the apparatus of FIG. 2 partially folded up for carrying.
Figure 7:
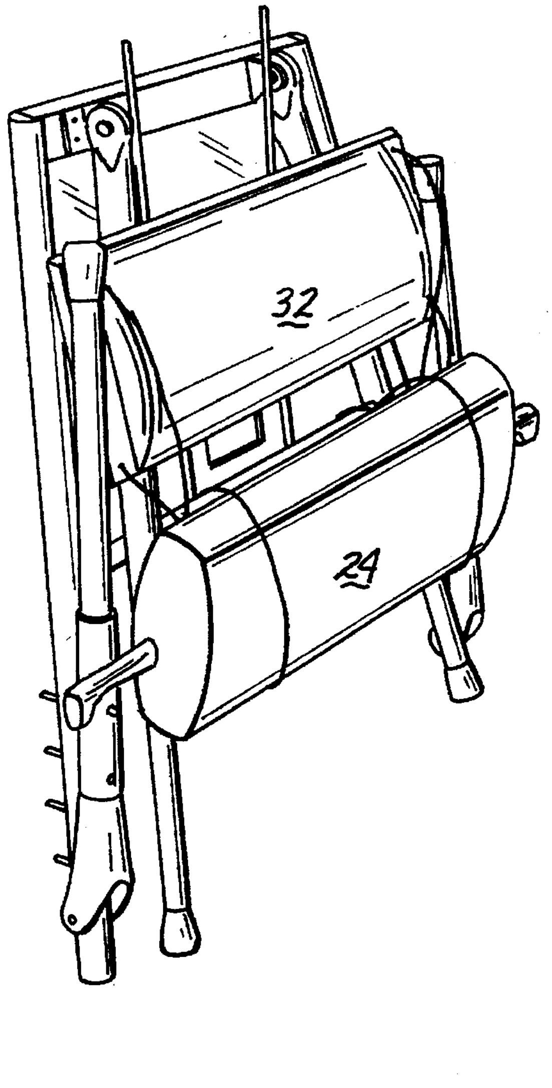
FIG. 7 is similar to FIG. 6 but shows the apparatus completely folded up for carrying purposes.

While the apparatus of the present invention could be set up permanently in the full position shown in FIG. 1, or only partially, as shown in FIG. 3, a principal advantage of the apparatus is that it may be folded up in the manner illustrated in FIGS. 6 and 7. Thus, the legs 20*a*, 20*b*, and 22*a* and 22*b* may first be folded up adjacent the side members 12*a* and 12*b*, respectively. The seat 42 may brought against the folded legs 20*a* and 20*b* and secured thereby by the cables 36 of the knee support member 32. The face support 28 may be tucked in between the folded legs 22*a* and 22*b*, while the larger cushions 38 and 40 may be carried separately, or simply attached to the apparatus.

From the foregoing description, it may be seen that the apparatus of the present invention lends itself to particular use by a masseur who is called upon to visit clients in their own homes or offices. The apparatus may be fabricated of rigid elements of either metal or plastic, preferably of light weight. The entire apparatus, thus, may weigh less than 15 lbs, inclusive of the cushions 38 and 40. An apparatus of this light weight imposes a minimal burden upon a visiting masseur and may readily be set up for use with a patient, and taken down and carried away at the conclusion of the massage treatment.

I claim:

1. Apparatus for supporting a patient undergoing a massage, bodywork or other type of physical therapy above a floor surface, said apparatus comprising:

a frame, said frame being formed by a first pair of similar rectilinear side members spaced from each other and laterally co-aligned in a common plane, each side member having a first forward end and second after end; and a pair of parallel first and second transverse members, also spaced from each other, each transverse member also having a first end and second end, the first and second ends of the first transverse member being secured to, and to extend between, the first ends of the side members, to join and retain said first ends of the side members in a fixed spaced apart relationship to each other; and the first and second ends of the second transverse member being secured to the side members, each forming a junction therewith, intermediate of the first and second ends of the side members equidistantly from the first transverse member, thereby to leave a portion of each of said side members extending rearwardly beyond the junction of the ends of the second transverse member with the side members; said first and second transverse members and the portions of the side members extending between the first and second transverse members defining a planar area;

a first pair of legs, one end of each leg being hingedly connected adjacent the first end of one of the side members to swing between a first position adjacent said one side member and a second position extending downwardly below said one side member to support the frame above the floor surface;

a second pair of legs, each leg being hingedly connected to the second end of a side member to swing between a first position in substantial abutment with a side member and a second position extending downwardly below the last said side member to support the frame above the floor surface;

substantially planar means disposed to cover the planar area between the side members and the transverse members, and said planar means being supported by the side members;

and a patient knee support comprising a horizontal planar member of a predetermined width and length with a pair of laterally extending opposite ends, said member having an area greater than would be occupied by a person's knees, said member being suspended above the floor surface by first and second flexible elements each having a first and second end, each of said flexible elements being looped over the second transverse member of the frame and having its first and second ends spaced apart from each other and secured to one of the laterally extending ends of the knee support;

whereby a patient may be positioned for massage treatment of the back, shoulder and neck areas by kneeling on the knee support member and bending over the second transverse member to rest on the planar members supported between the side members and the first and second transverse members.

2. The apparatus as described in claim 1 wherein there is also provided a face supporting member extending horizontally and forwardly from the first transverse member and supported by the first transverse member.

3. The apparatus as described in claim 2 wherein a transverse element is secured between the first pair of legs intermediate the ends of the legs, adapted to provide a hand support when a patient is placed in a position to dispose his or her chest on the planar means and his or her face on the face supporting member.

4. The apparatus as described in claim 2 wherein cushions are placed upon the supports for the patient's chest and head.

5. The apparatus as described in claim 1 wherein there are provided on the portion of each side member which extends rearwardly beyond the junction of the second traverse member with a side member, a plurality of upwardly extending elements spaced similarly from each other on each side member to constitute a corresponding oppositely disposed pair of upwardly extending elements so that a transverse shaft laid across the pair of side members and between similarly disposed upwardly extending elements, will be parallel to the second transverse member extending between the side members.

6. The apparatus as described in claim 5 wherein a cushioned rectangular member is provided, said cushioned rectangular member having a rigid shaft extending centrally and axially through the cushioned member and beyond each end thereof to constitute an axial extension, whereby said rectangular member may be disposed at any of a plurality of transverse locations between the side members by laying the axial end extensions of the shaft across the side members between any of the corresponding oppositely disposed pairs of upwardly extending elements on portions of each side member which extends rearwardly beyond the second transverse member with a side member.

7. The apparatus as described in claim 4 wherein a lower body support frame is provided to be removably mounted adjacent the after ends of the side members, said lower body support frame comprising a pair of similar arched rigid elements spaced from each other in parallel and secured in such relationship by a plurality of transverse elements spaced from each other and disposed in parallel, each of said arched elements having a forward end and an after end, the forward end of each of the arched members being provided with means removably to secure said end to the after end of a side member and at a predetermined height in relation to said after end of the side member to which it is secured.

8. The apparatus as described in claim 7 wherein the means removably to secure the forward end of each arched member to the second after end of a side member, comprises a flexible loop, one part of which is secured to said forward end with the loop adapted to be placed over any one or more of the upwardly extending elements on the side member extensions to adjust the height of the forward end of the arched side members.

9. The apparatus as described in claim 1 wherein the height of each end of the legs is adjustable and securable temporarily at any height selectable.

10. Apparatus for supporting a patient undergoing a massage, bodywork or other type of physical therapy above a floor surface, said apparatus comprising:

a frame, said frame being formed by a first pair of similar rectilinear side members spaced from each other and laterally coaligned in a common plane, each side member having a first forward end and second after end; and a pair of parallel first and second transverse members, also spaced from each other, each transverse member also having a first end and a second end, the first and second ends of the first transverse member being secured to, and extending between, the first ends of the side members, to join and retain said first ends of the side members in a fixed spaced apart relationship to each other; and the first and second ends of the second transverse member being secured each to form a junction, intermediate of the first and second ends of the side members equidistantly from the other transverse member, thereby to leave a portion of each of said side members extending rearwardly beyond the junction of an end of the second transverse member with a side member;

Said first and second transverse members and the portions of the side members extending between the first and second transverse members defining a planar area;

a first pair of legs, one end of each leg being hingedly connected adjacent the first end of one of the side members to swing between a first position adjacent said one side member and a second position extending downwardly below said one side member to support the frame above the floor surface.

a second pair of legs, each leg being hingedly connected to the second end of a side member to swing between a first position in substantial abutment with a side member and a second position extending downwardly below the last said side member to support the frame above the floor surface;

substantially planar means disposed to cover the planar area between the side members and the transverse members, and supported by the side members;

the portions of the side members extending rearwardly beyond the junctions of the second transverse member with the side members, having a plurality of upwardly extending elements similarly spaced from each other; and a lower body support frame, said lower body support frame comprising a pair of similar arched rigid elements spaced from each other in parallel and secured in such relationship by plurality of transverse elements spaced from each other and disposed in parallel, each of said arched elements having a forward end and an after end, the forward end of each of the arched members being provided with means removably to secure said forward end to the after end of one of the two side members.

* * * * *